United States Patent
Bozigian et al.

[19]

[11] Patent Number: 5,977,428
[45] Date of Patent: Nov. 2, 1999

[54] ABSORBENT HYDROGEL PARTICLES AND USE THEREOF IN WOUND DRESSINGS

[75] Inventors: Haig P. Bozigian, Encinitas, Calif.; Guy Gendron, Seattle; Janelle Roberts, Kirkland, both of Wash.

[73] Assignee: ProCyte Corporation, Redmond, Wash.

[21] Appl. No.: 08/794,563

[22] Filed: Feb. 3, 1997

Related U.S. Application Data

[60] Provisional application No. 60/033,630, Dec. 20, 1996.

[51] Int. Cl.$^6$ ...................................................... A61F 13/00
[52] U.S. Cl. ................................ 602/48; 602/41; 602/79; 602/56; 128/156
[58] Field of Search ................................ 602/48, 46, 41, 602/79, 56; 128/156

[56] References Cited

U.S. PATENT DOCUMENTS

| | | | |
|---|---|---|---|
| 4,664,662 | 5/1987 | Webster | 604/369 |
| 4,909,244 | 3/1990 | Quanfoot et al. | 128/156 |
| 4,943,618 | 7/1990 | Stoz et al. | |

FOREIGN PATENT DOCUMENTS

| | | |
|---|---|---|
| 171 268 A2 | 2/1986 | European Pat. Off. |
| 282 316 A2 | 9/1988 | European Pat. Off. |
| 302 536 A1 | 2/1989 | European Pat. Off. |
| 575 090 A1 | 12/1993 | European Pat. Off. |
| 2 194 144 | 3/1988 | United Kingdom. |
| WO 88/08310 | 11/1988 | WIPO. |
| WO 93/06802 | 4/1993 | WIPO. |
| WO 96/04025 | 2/1996 | WIPO. |

OTHER PUBLICATIONS

Westerhof et al., "Cleaning of chronic recalcitrant wounds with polysaccharide pads," *Phlebol* 23(5): 156–160, 1994.
Szycher et al., "Modern Wound Dressings: A Systematic Approach to Wound Healing," *J. Biomater. Appl.* 7: 142–213, 1992.

*Primary Examiner*—John G. Weiss
*Assistant Examiner*—Kelvin Hart
*Attorney, Agent, or Firm*—Seed and Berry LLP

[57] ABSTRACT

An absorbent dressing for absorbing exudate from a wound is disclosed. The absorbent dressing contains a plurality of dried absorbent hydrogel particles sealed within a porous container. The porous container is non-adherent to the wound, and the hydrogel particles remained sealed within the container after absorbing the wound exudate. In a preferred embodiment, the particles are dried polyacrylonitrile hydrogel particles, and the porous container is in the form of a sachet bag made from nylon, cotton, polyester, polypropylene and the like.

28 Claims, 6 Drawing Sheets

Representative polyethylene mesh sachet containing dried hydrogel particles product of the invention

Fig. 1

Representative cyllinder shaped dried hydrogel particle

Fig. 2

Representative polyethylene mesh sachet containing dried hydrogel particles product of the invention

Fig. 3

Time Course of Saline Absorption by Polyethylene Sachet Containing Highly Absorbent Hydrogel Particles

Fig. 4

Time Course of Saline Absorption Sachet Containing Absorbent Hydrogel Particles combined with Binding Agents and Plasticizers — Amylopectin and Glycerin

Fig. 5

Time Course of Saline Absorption Sachet Containing Absorbent Hydrogel Particles combined with Binding Agents and Plasticizers — Sucrose and Glycerin

Fig. 6

ABSORBENT HYDROGEL PARTICLES AND USE THEREOF IN WOUND DRESSINGS

CROSS REFERENCE TO RELATED APPLICATION

This application claims benefit from U.S. Provisional Application No. 60/033,630, filed Dec. 20, 1996.

TECHNICAL FIELD

This invention relates to dried hydrogel particles contained in a porous container for absorbing wound exudate, to manage fluid in wounds and/or to maintain an optimal healing environment.

BACKGROUND OF THE INVENTION

Dermal wound healing is a natural process which occurs whenever there is a break in the surface of the skin. An orderly, progressive process begins to take place in several stages, commencing with an inflammatory response necessary for natural sterilization of the area, clotting, and preparation of the wound for its natural progress toward closure.

The second stage of wound repair primarily involves migration of necessary cells to the wound site. These cells, which also appear in an ordered sequence during the second stage of healing, include key white cells, followed by polymorphonuclear leukocytes and macrophages—all essential to initiation of the repair process. These cells serve to clean up the wound and to deliver an endogenous mixture of growth factors to the wound site. In addition to white cells, fibroblasts from the wound periphery migrate to and into the site to deposit collagen, glycosaminoglycans, and other extracellular matrix components, providing the basis for granulation tissue formation. These macromolecules, in conjunction with capillary endothelial cells and new blood vessels, form the new tissue required to repair the defect.

The third stage of dermal wound healing involves proliferation of the cell types mentioned above together with subsequent increases in the amount of granulation tissue and coverage of the area with new epithelium.

Throughout the healing process, wounds produce a variety of fluids, generally known as wound exudate. The composition and quantity of this exudate may differ by wound type and with each stage of the wound's healing process. Exudate may vary—consisting primarily of blood and serous fluids to highly concentrated protein solutions. In general, wound exudate provides the necessary source of growth factors, nutrients and cells that are essential to the wound repair process. However, as with many biological processes, the amount of wound exudate must be controlled because over-production can provide a media for bacterial proliferation or lead to maceration of the surrounding healthy tissue. Conversely, inadequate types or amounts of wound exudate, or drying of the wound fluid, will lead to scab formation and impaired wound healing.

The control of wound exudate, referred to as moisture control, has become a major focus in current wound dressing design. The major categories of moist or synthetic wound dressings currently in use are thin films, hydrocolloids, hydrogels, and alginates. All of these various types of dressings control wound exudate through combinations of absorption, moisturization, and moisture permeability. The overall aim of moist wound dressings is to maintain the appropriate balance of moisture in the wound environment, which is essential to allow the natural wound healing process to occur.

Wound dressings which maintain a moist wound environment range from gels to thin films, foams, alginates, and hydrocolloids (see, e.g., Szycher et al., *J. Biomater. Appl.* 7:142–213, 1992). Thin film wound dressings consist of synthetic polymeric films which have one side coated with a pressure sensitive adhesive. This type of wound dressing has little or no absorptive ability and manages moisture primarily by the moisture vapor permeability of the polymeric film. Pooling and concentration of wound exudate under these dressings is commonly observed.

Hydrocolloids is a term commonly used to describe a family of wound management products consisting of gel forming agents combined with elastomers and adhesives attached to a polyurethane film or foam. This type of dressing usually has poor moisture vapor permeability, but some absorptive capability. These dressings typically absorb wound exudate by becoming thicker and forming a gelatinous material over the wound which has to be washed from the wound at each dressing change.

Hydrogel wound dressings are sheet dressings often supplied with an impermeable polymeric backing sheet. The presence of the backing sheet prevents the partially hydrated hydrogel from dehydrating and drying onto the wound bed. The hydrogels are similar to the hydrocolloids in their ability to absorb and manage wound exudate. Generally, hydrogel dressings do not dissolve into the wound bed as do hydrocolloids.

Foam dressings are generally manufactured from polymeric materials such as hydrophylic polyurethane. These foams contain open cells facing the wound surface which serve to absorb wound exudate by a sponge type mechanism. As with all sponges, the absorbed exudate is not tightly bound in the foam and a certain amount can be "squeezed" from the dressing upon removal.

Alginates are highly absorbent wound dressings composed of a variety of alginic acids extracted from certain species of seaweeds. The addition of a calcium salt during processing allows the formation of insoluble fibers which can be woven or formed into wound dressings of various sizes and shapes. During use, alginate wound dressing typically swell and form a soft gel in the wound bed. This gel must be washed from the wound bed at each dressing change.

In addition to the above, EP-A1-0 171 268 discloses a dressing for use in deep wounds which comprises small pieces of absorbent polyurethane foam contained within a porous bag or sachet. In a similar manner, EP-A1-0 575 090 discloses products suitable for absorbing wound exudate comprising particles of alginate or alginic acid enclosed in perforated bags.

Despite the wide variety of wound dressings available, chronic wounds are still a serious medical situation and there is a need for advanced wound care dressings which manage the moist wound environment. This includes the need for moisture controlling and absorbing wound dressings which do not leave a residue in the wound bed and which retain fluid when removed. The present invention fulfills these needs and provides further related advantages.

SUMMARY OF THE INVENTION

Briefly stated, this invention generally relates to the management of the wound environment by the absorption of excess exudate by dried hydrogel particles. In particular, the application of such absorbent dried hydrogel particles, contained in a non-adherent porous pouch or sachet, allows easy application and removal of the absorbent particles from the wound bed, as well as easy access of the particles to the wound exudate. Hydrogels are cross-linked water swollen polymers having a water content ranging from 30% to 90% or greater depending on the type of polymer used.

In one aspect of the invention, dried hydrogel particles are prepared by base hydrolysis of polyacrylonitrile aquagel followed by neutralization and drying essentially as disclosed in U.S. Pat. No. 4,943,618 to Stoy et al (hereby incorporated by reference). The dried hydrogel particles are packaged in sachets formed by heat sealing porous sheets of low density polyethylene or similar polymeric material. The polyethylene mesh is such that the openings are large enough to allow fluid transfer, but small enough to contain the absorbent particles. In addition, the amount of absorbent particles is such that, if the maximal amount of fluid is absorbed by the particles, the particles do not cause rupture of the sachet. Sachets formed in this manner absorb saline at 2–50 times their weight. In a preferred embodiment of the invention, the particles absorb about 10–30 times their weight in saline.

In another aspect of the invention, absorbent dried hydrogel particles are sealed in sachets formed from an acceptable medical grade of nylon mesh. Sachets may also be formed from any type of porous material such as non-woven or woven cotton gauze, polyester mesh, polypropylene and polyvinyl acetate.

The non-adherent porous pouch or sachet containing the absorbent dried hydrogel particles of this invention may comprise multiple parts or pockets. For example, these could comprise dressings with two rows of two individual sachets, or one row with multiple individual linked sachets. The sizes of the individual sachets are chosen to fit within specific sizes or types of wounds.

In another aspect of this invention, the non-adherent porous pouch or sachet containing the absorbent dried hydrogel particles of this invention may comprise part of a larger wound dressing. In this aspect, the non-adherent porous pouch or sachet containing the absorbent dried hydrogel particles would serve as the part of a wound dressing which would absorb wound exudate, while other parts would serve to keep the sachet in place and to protect the wound.

The absorbent dried hydrogel particles can take various forms such as granules, cylindrical pellets, spheres, or spheroids. Such particles can be ground to a fine powder and still contained within the sachet as long as the perforations in the bag are smaller than the diameter of the particles contained therein.

In another aspect of the invention, absorbent hydrogel particles can be ground to a fine powder, mixed with binders and plasticizers and pressed into sheets. Such sheets can then be encased in porous mesh to form pouches or sachets. Although the initial size of the powdered absorbent dried hydrogel particles prepared in this aspect of the invention may be smaller than the perforations in the bag when they are dry, upon absorption of wound exudate, the hydrogel particles swell such that their diameter is greater than the perforations in the pouch material. The small size of the absorbent dried hydrogel particles in powdered from results in very rapid fluid absorption.

The combination of the absorbent dried hydrogel with a variety of other materials (binders) and plasticizers forms a matrix in which the absorbent is evenly distributed. The matrix allows moisture to wick rapidly to the interior of absorbent by exposing the maximal surface of the absorbent particle to moisture. This allows a much higher rate of absorption associated with high surface area while obviating the difficulties of handling/packaging fine absorbent powders. The material may be molded to almost any shape.

In another aspect of the invention, the absorbent particles of the invention may contain or release wound healing agents or nutrients which wound aid the healing process or maintain an optimal healing environment. Such agents would be, for example, growth factors, antiseptic and antimicrobial agents, vitamins, and/or micronutrients such as copper or zinc. The absorbent particles of the invention may also contain or release agents to control odor in the wound or to control infection in the wound. Examples would be activated charcoal, antibiotics and antifungals.

Other aspects of this invention will be apparent from the following detailed description and attached drawings.

DETAILED DESCRIPTION OF THE INVENTION

As mentioned above, this invention is generally directed to management of the wound environment by absorption of excess exudate with absorbent dried hydrogel particles. In a preferred aspect of this invention the absorbent dried hydrogel particles of the invention are prepared by base hydrolysis of polyacrylonitrile aquagel followed by neutralization and drying essentially as described in U.S. Pat. No. 4,943,618 to Stoy et al. Aquagel is a solid form of polyacrylonitrile (PAN) formed by extrusion of a 15% solution of PAN dissolved in 55% NaSCN into a large excess of distilled water. This extrusion process results in the formation of apparently solid pellets of PAN containing 69–75% water. This form of PAN, termed an aquagel, is composed of alternating domains of "crystalline" PAN and "amorphous" domains in which the PAN chains are held apart by water filled voids.

One preferred dried hydrogel particle of this invention is a base hydrolysis product of PAN aquagel which absorbs approximately 50–60 times its weight in excess saline. The general preparation procedure is summarized as follows:

| PAN Source | Aquagel Noodles, or Pellets, or beads |
|---|---|
| NaOH Concentration | 4.5% |
| Temperature | 19–23° C. |

-continued

| PAN Source | Aquagel Noodles, or Pellets, or beads |
|---|---|
| Quench Point, $Wt_{final}/Wt_{initial}$ | 11.9–12.0 |
| Hydrolysis Time | 115 hours |
| Salt Form | Ammonium Salt |

The aquagel pellets are incubated in the NaOH solution under the above conditions. The extent of the hydrolysis of the nitrile groups in the "amorphous" domains is monitored by the weight gain of the aquagel as hydrolysis results in polymer structures which swell in an aqueous environment. This swelling is monitored as a ratio of the weight at time t ($Wt_{time\ t}$) to the initial weight ($Wt_{initial}$). The reaction quench point is the swelling or weight gain ratio as described above. After the desired quench point swelling of 11.9 to 12.0 was achieved, the reaction was terminated by the addition of cold dilute sulfuric acid. The hydrogel pellets were washed extensively with distilled water followed by soaking in 12% ammonium bicarbonate solution. The resultant pellets were placed in a 60° C. oven until dried.

Another preferred dried hydrogel product of this invention is prepared by a procedure similar to the above, except that the swelling target quench factor is 6.0. The general preparation procedure is summarized as follows:

| PAN Source | Aquagel Noodles, or Pellets, or Beads |
|---|---|
| NaOH Concentration | 4.5% |
| Temperature | 30.0–31.0° C. |
| Quench Point, $Wt_{final}/Wt_{initial}$ | 6.0 ± 0.2 |
| Hydrolysis Time | 29–30 hours |
| Salt Form | Ammonium Salt |

After the desired quench point swelling of 6.0 is achieved, the reaction is terminated by the addition of cold dilute sulfuric acid. The hydrogel pellets are washed extensively with distilled water followed by soaking in 12% ammonium bicarbonate solution. The resultant pellets are placed in a 60° C. oven until dried.

Other embodiments of the invention are absorbent dried hydrogel particles prepared by the above procedures to quench point swelling of 4 to 8.

The shape and size of the starting aquagel particles determine the shape and size of the dried hydrogel particles of this invention. Such absorbent dried hydrogel particles can take various forms, such as granules, cylindrical pellets, spheres, and spheroids.

In a preferred embodiment of this invention, the dried hydrogel particles are small cylinders approximately 0.5–2 mm in length with a diameter of approximately 1 mm. A more preferred embodiment is small spherical particles 0.5–2 mm in diameter.

Other hydrogels can also be used in this invention to form absorbent dried hydrogel particles. Examples of hydrogels which could be dried are those prepared from polyacrylic acids, polyacrylamides, poly-2-hydroxyethyl methacrylate, poly ethyl methacrylate, poly-propylene glycol methacrylate, poly-N-vinylpyrrolidone, poly methyl methacrylate, poly glycidyl methacrylate, poly-glycol methacrylate, absorbent silicones, and absorbent polyurethanes. The process of drying and forming absorbent dried hydrogel particles from the above hydrogels are known to those skilled in this field.

Preferred embodiments of this invention are dried hydrogel particles encased in square, rectangular, circular, or oval porous polyethylene sachets. Such porous sachets are divided by heat seals into multiple individual pouches containing dried hydrogel particles depending on the size of the sachet. A description of preferred sizes and shapes for sachet dressings is shown below.

| 5 in × 5 in | Two rows of two pouches each |
|---|---|
| 4 in × 4 in | Two rows of two pouches each |
| 3 in × 3 in | Two rows of two pouches each |
| 2 in × 2 in | Two rows of two pouches each |
| 1.5 in × 3 in | One row of two pouches |
| 0.75 in × 6 in | One row of three pouches |

The individual sachet s of this invention can be manufactured with either square corners or round corners. In a preferred embodiment the smaller sizes of sachets of this invention could also include a "tail" or handle composed of the same or similar porous polyethylene mesh. Such a handle serves to facilitate removal of the absorbent sachet from the wound bed.

In addition to porous polyethylene and nylon, other materials may also be used to form the sachet pouches of this invention. Examples of preferred materials are shown below:

Woven and non-woven polypropylene
porous Low density polyethylene
Woven and non-woven polyester and derivatives
Woven and non-woven nylon
Woven and non-woven rayon
Woven and non-woven cotton
Woven and non-woven other materials
Woven and non-woven blends of the above
LDPE laminates of the above
Porous PTFE laminates of the above
Polyethylene oxide gels
Thin hydrogel sheets
Other moisture transparent polymer sheets
Other moisture transparent egls
LDPE mesh
other polymeric mesh
hydrophilic polyurethanes In another embodiment, the absorbent dried hydrogel particles encased in porous polyethylene or nylon pouches absorb an amount of wound exudate in 24 hours such that the wound exudate would not migrate beyond the bounds of the dressing.

In another embodiment of this invention, the absorbent hydrogel particles are ground to a fine powder, mixed with binders and plasticizers and pressed into sheets or other shapes such as spheres. Such sheets are then encased in the porous mesh sachets of the invention. The small size of the dried hydrogel particles in powdered form results in very rapid fluid absorption while the binders and plasticizers serve to maintain the powdered hydrogel within the porous sachet.

Preferred binding agents and plasticizers which can be mixed with the powdered dried hydrogel particles are shown below.

| Binders | Plasticizers |
| --- | --- |
| Sucrose | Glycerin |
| Carageenan | PEG 200 |
| Sodium and Calcium Alginates | PEG 400 |
| Gum Arabic | PEG 600 |
| Corn starch | Propylene Glycol |
| Bovine Serum Albumin | Sorbitol |
| Fumed Silica | |
| Ethyl cellulose | |
| Methyl cellulose | |

Other binders and plasticizers within the scope of this invention are shown below.

| Binders | Plasticizers |
| --- | --- |
| Other Sugars | Other PEGs |
| Other Gums | Polyethylene oxide solutions |
| Other Starches | Polyethylene oxide gels |
| Other Proteins | Tripropylene glycol |
| Starch co-polymers | Corn oils |
| Gelatins | Vegetable oils |
| Pectins | Mineral oils |
| Carbomers, carbopols | |
| Polyhydroxyethyl methacrylate | |
| Aloe Vera | |
| Agars | |

In another embodiment of this invention, the non-adherent porous pouch or sachet containing the absorbent dried hydrogel particles of this invention may comprise part of a larger wound dressing. In this aspect, the non-adherent porous pouch or sachet containing the absorbent dried hydrogel particles would be attached to a sheet wound dressing. Such combination wound dressings are commonly called "island" dressings. The non-adherent porous pouch or sachet containing the absorbent dried hydrogel particles would serve to absorb wound exudate while the upper layer would serve to keep the sachet in place over the wound and to protect the wound from the environment. Examples of materials which can be used for island dressing outer layers are the following:

Polyurethane foams (open and closed cell)
Hydrophilic polyurethane foams (open and closed cell)
Other polymeric foam materials (open and closed cell)
Porous PTFE laminates of polymeric foams
Porous PTFE laminates of woven or non-woven nylon
Porous PTFE laminates of woven or non-woven polyester and derivatives
Porous PTFE laminates of woven or non-woven rayon
Porous PTFE laminates of woven or non-woven polypropylene
Porous PTFE laminates of low density polyethylene
Polyurethane sheets
Polyester sheets
Polyethylene sheets
Polypropylene sheets
Laminates of various rubbers and woven or non-woven nylon
Laminates of various rubbers and woven or non-woven nylon
Laminates of various rubbers and woven or non-woven polyester and derivatives
Laminates of various rubbers and woven or non-woven polypropylene
Laminates of various rubbers and low density polyethylene
Laminates of various rubbers and woven or non-woven rayons
Laminates of various rubbers and other fabrics
Laminates of various rubbers and polymeric foams
Spandex
Laminates of various materials on spandex In another embodiment of this invention, the non-adherent porous pouch or sachet containing the absorbent dried hydrogel particles of this invention may be coated with an acceptable medical grade adhesive to maintain the sachet in the wound.

The following examples are offered by way of illustration, and not by way of limitation.

EXAMPLES

The examples which follow illustrate the preparation, characterization and utility of certain exemplary embodiments of the present invention.

Example 1

Preparation of Highly Absorbent Dried Hydrogel Particles By Base Hydrolysis of Polyacrylonitrile One type of dried hydrogel particles of the invention are prepared by base hydrolysis of polyacrylonitrile aquagel (to a quench factor of 6.0) followed by neutralization and drying essentially as described in U.S. Pat. No. 4,943,618 to Stoy et al.

Figure 1:
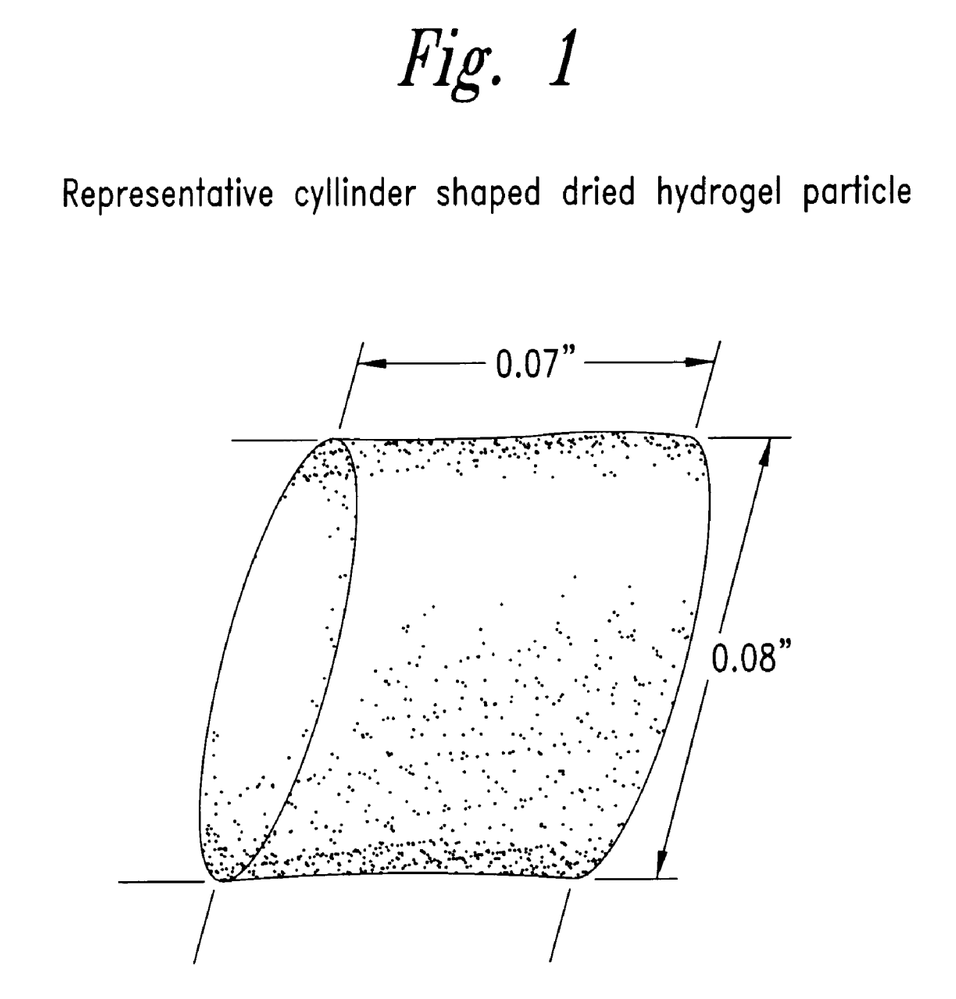
FIG. 1 illustrates a representative cylinder-shaped dried hydrogel particle.

Aquagel-15 pellets (2000 g) were rinsed and drained of excess water and then transferred to a plastic basket lined with polypropylene mesh. Approximately 20 pellets (0.1550 g) were blotted dry with a paper towel, weighed on an analytical balance and transferred to a probe container fabricated from a capped 15 ml Teflon centrifuge tube that had been uniformly pierced with ⅛" holes. The basket was placed into a Nalgene tank (50 L) containing a solution of 1010 g NaOH in 21.28 kg of deionized $H_2O$ at 30° C. The temperature of the reaction mixture was maintained at 30° C. by continuous recirculation of the sodium hydroxide solution through a stainless steel coil immersed in a 30° C. water bath using a small pump (10 gpm). The probe container was immersed in the sodium hydroxide solution and the timer was started. After approximately 30 minutes in the sodium hydroxide solution the pellets had turned a deep burgundy color. Monitoring of the probe weight was begun after a reaction time of approximately 20 hours. This was performed by removing the probe container from the sodium hydroxide solution, noting the time, blotting the pellets dry on a paper towel and then weighing the pellets on an analytical balance. When the pellets had reached a six-fold (6.0±0.2) increase in weight, the reaction was quenched by addition of a solution of 1728 g concentrated $H_2SO_4$ in 5174 g deionized water, which had been pre-equilibrated to 4° C. The quench reaction was allowed to proceed for 4 hours whereby the red color had disappeared from the center of the pellets when cut in half. The quench solution was drained off and the pellets were washed with deionized $H_2O$ with continuous overhead stirring until the pH was ≧5.0. The washed pellets were then added to a solution of 648 g of $NH_4HCO_3$ in 4.8 kg deionized $H_2O$ in a 50 L Nalgene tank and the neutralization reaction was allowed to proceed overnight at room temperature. After standing overnight the pellets had absorbed all of the liquid. The pellets were rinsed quickly with deionized $H_2O$ and then transferred to Pyrex trays for drying at 60° C. in a convection oven. Yield: 776 g of dried hydrogel pellets. A representative cylinder shaped highly absorbent hydrogel particles is shown and described in FIG. 1.

Another type of dried hydrogel particles of the invention are prepared by base hydrolysis of polyacrylonitrile aquagel to a quench factor of 12.0. Aquagel-15 pellets (1000 g) were rinsed and drained of excess water and then transferred to a plastic basket lined with polypropylene mesh. Approximately 22 pellets (0.1654 g) were blotted dry with a paper towel, weighed on an analytical balance and transferred to a probe container fabricated from a capped 15 ml Teflon centrifuge tube that had been uniformly pierced with 1/8" holes. The basket was placed into a Nalgene tank (50 L) containing a solution of 1010 g NaOH in 21.28 kg of deionized $H_2O$ at 35° C. The temperature of the reaction mixture was maintained at 35° C. by continuous recirculation of the sodium hydroxide solution through a stainless steel coil immersed in a 35° C. water bath using a small pump (10 gpm). The probe container was immersed in the sodium hydroxide solution and the timer was started. After approximately 30 minutes in the sodium hydroxide solution the pellets had turned a deep burgundy color. Monitoring of the probe weight was begun after a reaction time of approximately 20 hours. This was performed by removing the probe container from the sodium hydroxide solution, noting the time, blotting the pellets dry on a paper towel and then weighing the pellets on an analytical balance. When the pellets had reached a twelve-fold (12.0±0.2) increase in weight, the reaction was quenched by addition of a solution of 1728 g concentrated $H_2SO_4$ in 5174 g deionized water, which had been pre-equilibrated to 4° C. The quench reaction was allowed to proceed for 4 hours whereby the red color had disappeared from the center of the pellets when cut in half The quench solution was drained off and the pellets were washed with deionized $H_2O$ with continuous overhead stirring until the pH was ≧5.0. The washed pellets were then added to a solution of 324 g of $NH_4HCO_3$ in 2.4 kg deionized $H_2O$ in a 50 L Nalgene tank and the neutralization reaction was allowed to proceed overnight at room temperature. After standing overnight the pellets had absorbed all of the liquid. The pellets were rinsed quickly with deionized $H_2O$ and then transferred to Pyrex trays for drying at 60° C. in a convection oven. Yield: 325 g of dried hydrogel pellets.

Example 2

Preparation of Highly Absorbent Dried Hydrogel Articles Containing Micronutrient Copper Another dried hydrogel product of this invention was prepared by a procedure similar to example 1 with the quench factor of 6.0 except than a source of micronutrient copper was added to the hydrogel particles before drying.

Pellets were prepared from Aquagel-15 as described above except that the pellets were not neutralized with ammonium bicarbonate. The quenched and washed "acid-stage" pellets of hydrogel were stored at room temperature in deionized $H_2O$. To 121 g of the acid-stage pellets was added a solution of 8.5 g glycyl-L-histidyl-L-lysine copper complex and 81 g ammonium bicarbonate in 600 g deionized $H_2O$. This mixture was allowed to stand overnight at room temperature whereby all of the liquid had been absorbed. The blue pellets were transferred to Pyrex drying trays and dried at 60° C. in a convection oven. Yield: 92.4 g.

Example 3

Polyethylene Sachet Containing Highly Absorbent Hydrogel Particles

Figure 2:
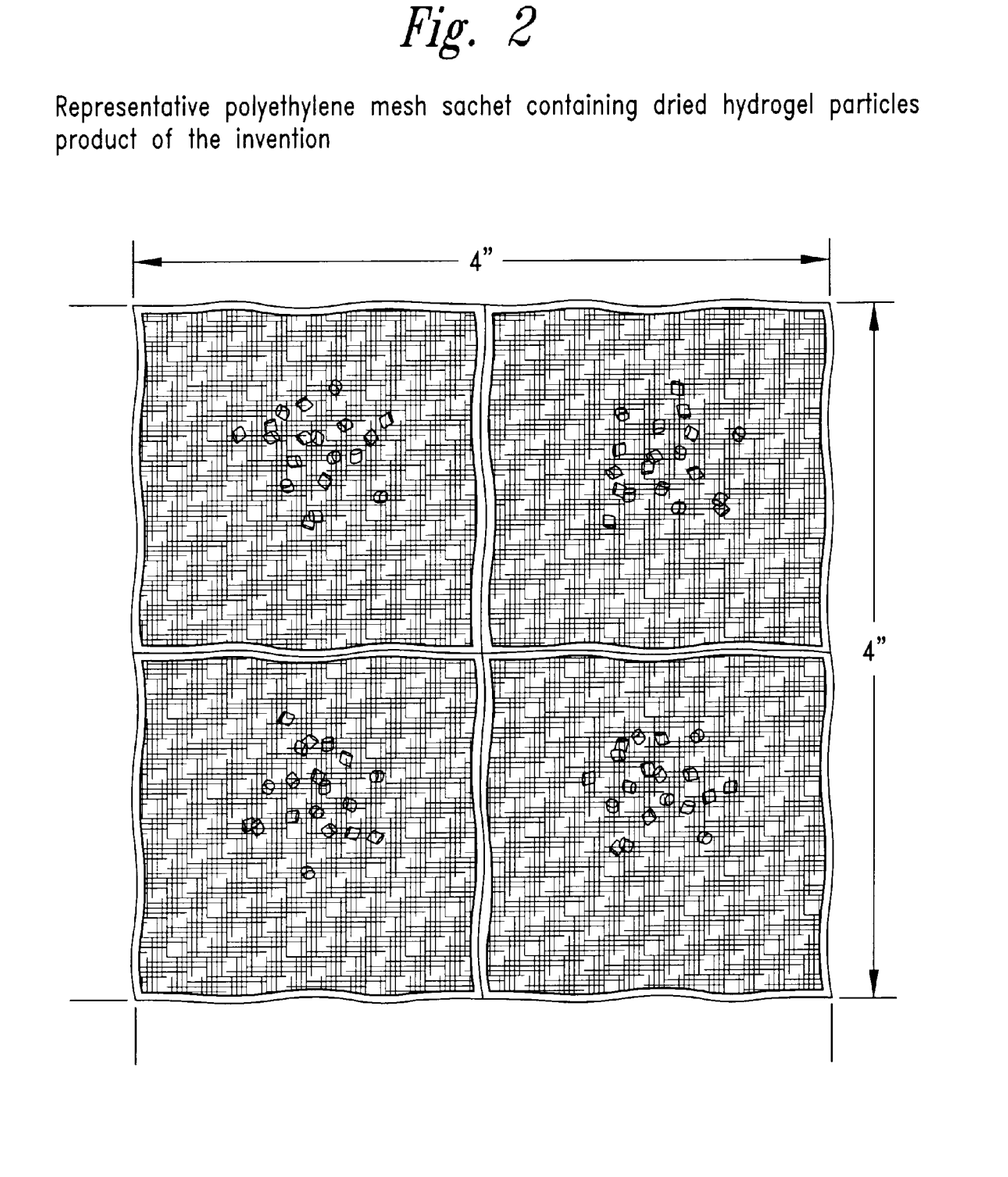
FIG. 2 illustrates a representative polyethylene mesh sachet of this invention.

A Polyethylene sachet containing highly absorbent hydrogel particles is shown and described in FIG. 2. The sachet outer material is a low density polyethylene mesh (LDPE).

Sheets of porous polyethylene mesh were cut to the desired sizes and three sides were heat sealed to form a pouch with one open side. The necessary weight of dried hydrogel particles were weighed out and added to the sachet and the top portion of the sachet heat sealed. Representative sachet dressings of the following dimensions were prepared: 4 inch X 4 inch (4 packets), 3 inch X 3 inch (4 packets), 4.5 inch X 1 inch (2 packets, 1 empty), and 0.65 inch X 4.5 inch with 3 packets.

Example 4

Saline Absorption By a Polyethylene Sachet Containing Highly Absorbent Hydrogel Particles One method to demonstrate utility of absorbent wound dressings of this invention is to determine the amount of 0.9% NaCl (Saline) which is absorbed by the dressing over time. Saline absorption can be determined by placing the sample in a large excess of 0.9% NaCl at room temperature. Absorption is determined by the weight gain of the invention after removal of surface moisture. Samples are incubated in the saline solution for up to 24 hours or until a constant weight gain is recorded. Milliliters of saline absorbed is calculated by subtracting the initial weight of the dressings from the weight at the specified time point.

Representative sachet dressings of the following dimensions were prepared as described in Example 2 and tested: 4 inch X 4 inch (4 packets), 3 inch X 3 inch (4 packets), 4.5 inch X 1 inch (2 packets, 1 empty), and 0.65 inch X 4.5 inch with 3 packets.

Figure 3:
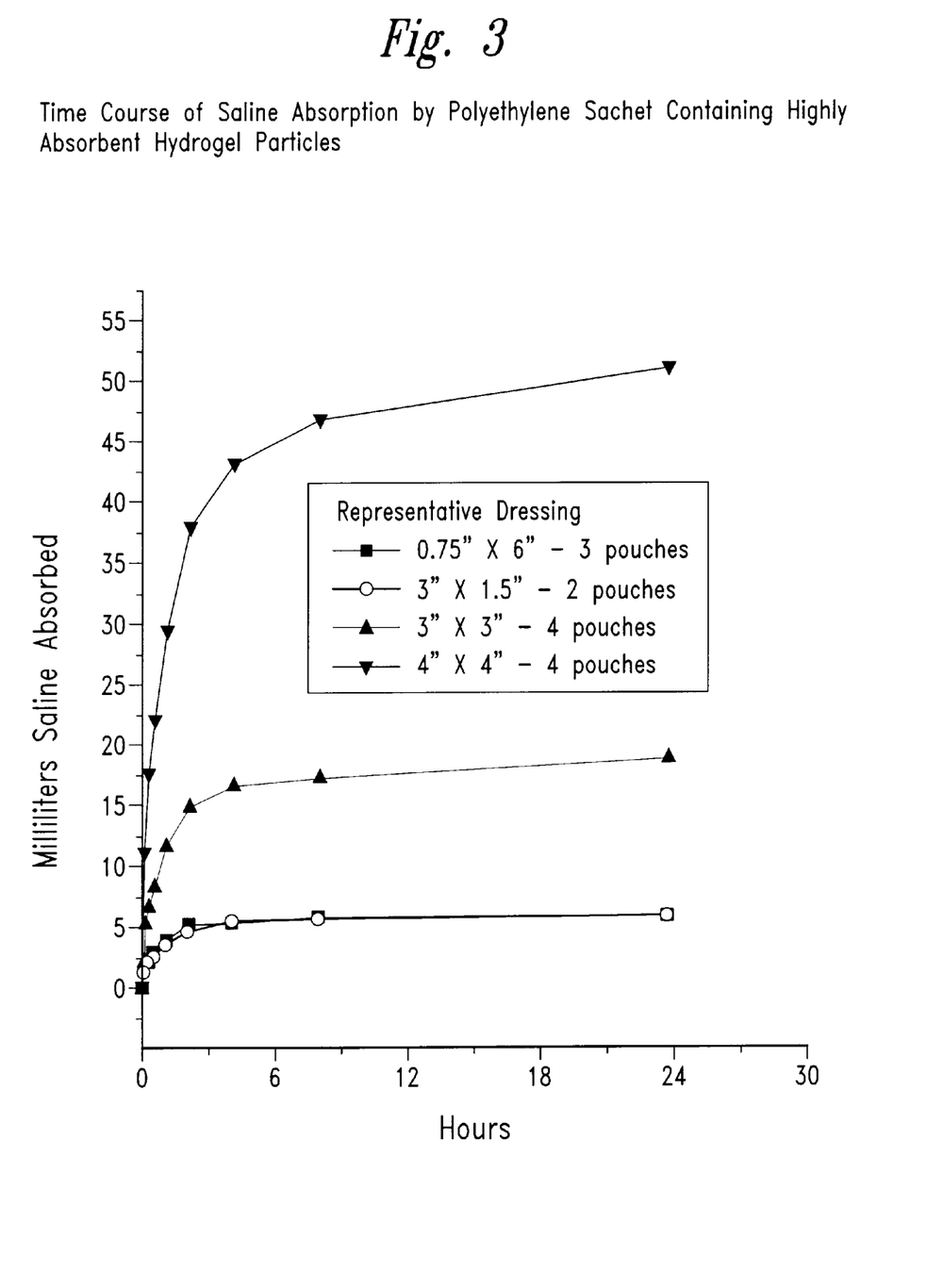
FIG. 3 is a graph showing the time course of saline absorption by a polyethylene sachet containing highly absorbent hydrogel particles.

The time course of saline absorption under the test conditions for all sizes of sachets containing a dried hydrogel is shown in FIG. 3. The maximal absorption ranged from about 5 to 50 milliliters. The dressings absorbed 20–25% of their maximal absorption within the first 5 minutes, the first time point taken.

Example 5

Sachet Containing Absorbent Hydrogel Particles Combined With Binding Agents and Plasticizers An absorbent hydrogel sheet was prepared by first mixing 10.00 g finely ground dried hydrogel material of Example 1 with 6.01 g powdered amylose-amylopectin (corn starch). These blended powders were then combined with 11.99 g glycerin with stirring. After a homogenous mixture was obtained a fraction of the slurry was sandwiched between two layers of silicone treated paper and cured at 75° C. for 25 minutes.

Figure 4:
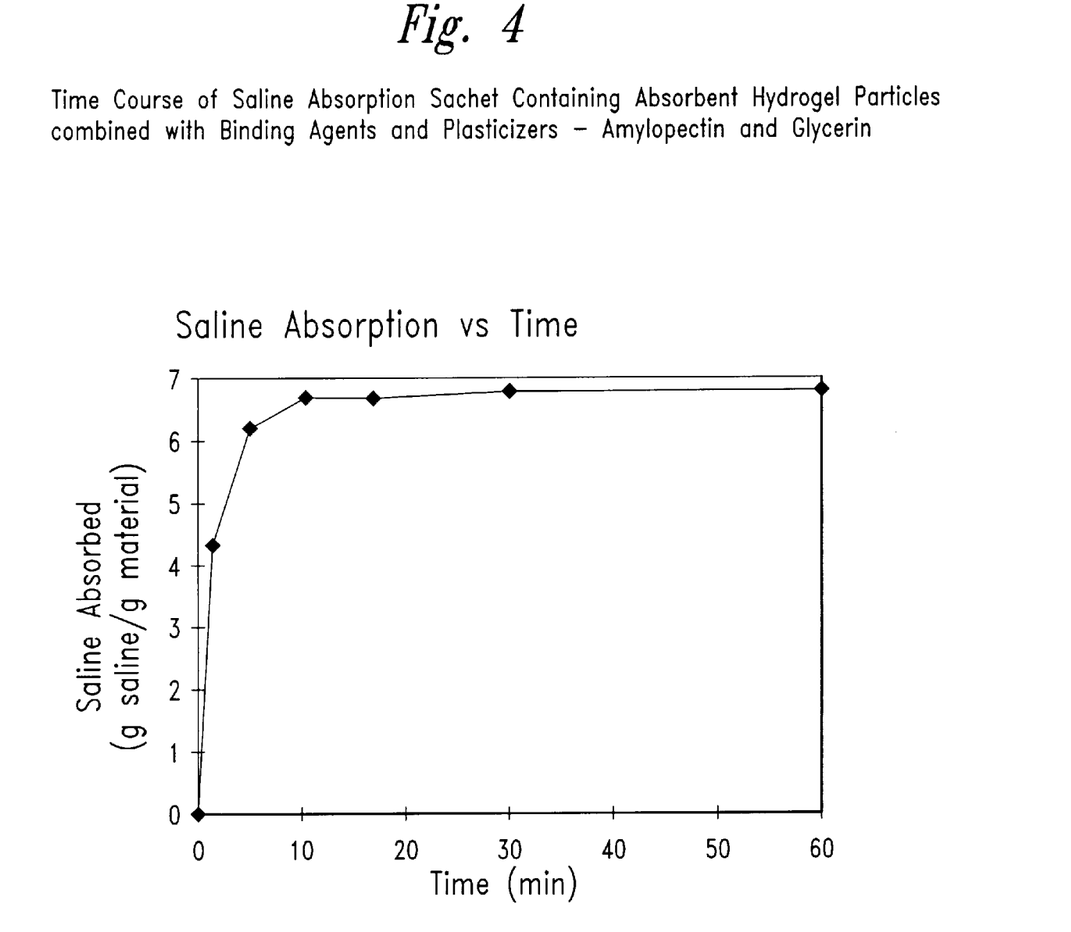
FIG. 4 is a graph showing the time course of saline absorption by a sachet containing absorbent hydrogel particles combined with binding agents and plasticizers (amylopectin and glycerin).

The resultant wafer was then weighed and heat sealed in a non-woven nylon mesh bag large enough such that upon swelling of the polymer it would not be full. The sample was then immersed in 0.9% NaCl. Weights after squeezing out entrapped water were obtained over time. Weights minus the bag weights were used for data analysis. See FIG. 4 which shows the saline absorption over time.

A further absorbent hydrogel sheet was prepared by first mixing 6.92 g finely ground dried hydrogel material of Example 1 with 6.92 g powdered sucrose. These blended powders were then combined with 4.45 g glycerin with stirring. After a homogenous mixture was obtained a fraction of the slurry was sandwiched between two layers of silicone treated paper and cured at 75° C. for 2.5 hours.

Figure 5:
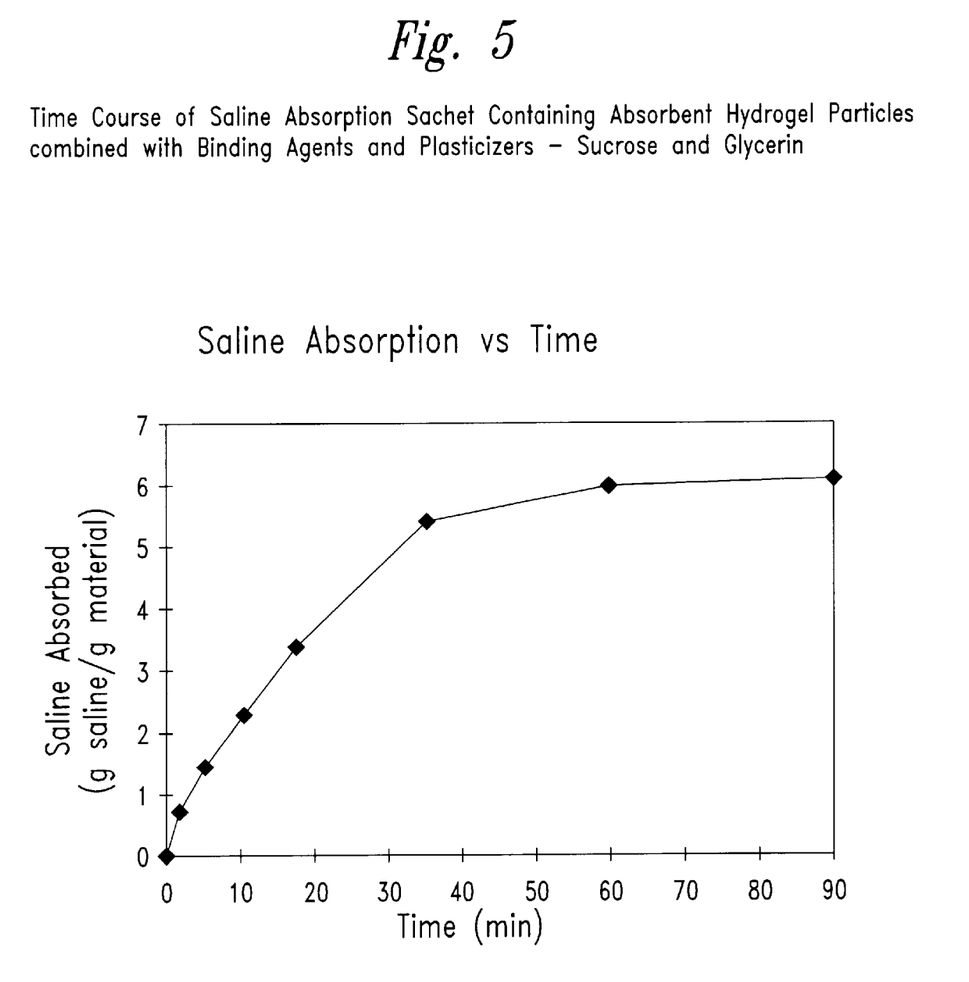
FIG. 5 is a graph showing the time course of saline absorption by a sachet containing absorbent hydrogel particles combined with binding agents and plasticizers (sucrose and glycerin).

The resultant wafer was then weighed and heat sealed in a non-woven nylon mesh bag large enough such that upon swelling of the polymer it would not be full. The sample was then immersed in 0.9% NaCl. Weights after squeezing out entrapped water were obtained over time. Weights minus the bag weights were used for data analysis. See FIG. 5 which shows the saline absorption over time.

Example 6

Figure 6:
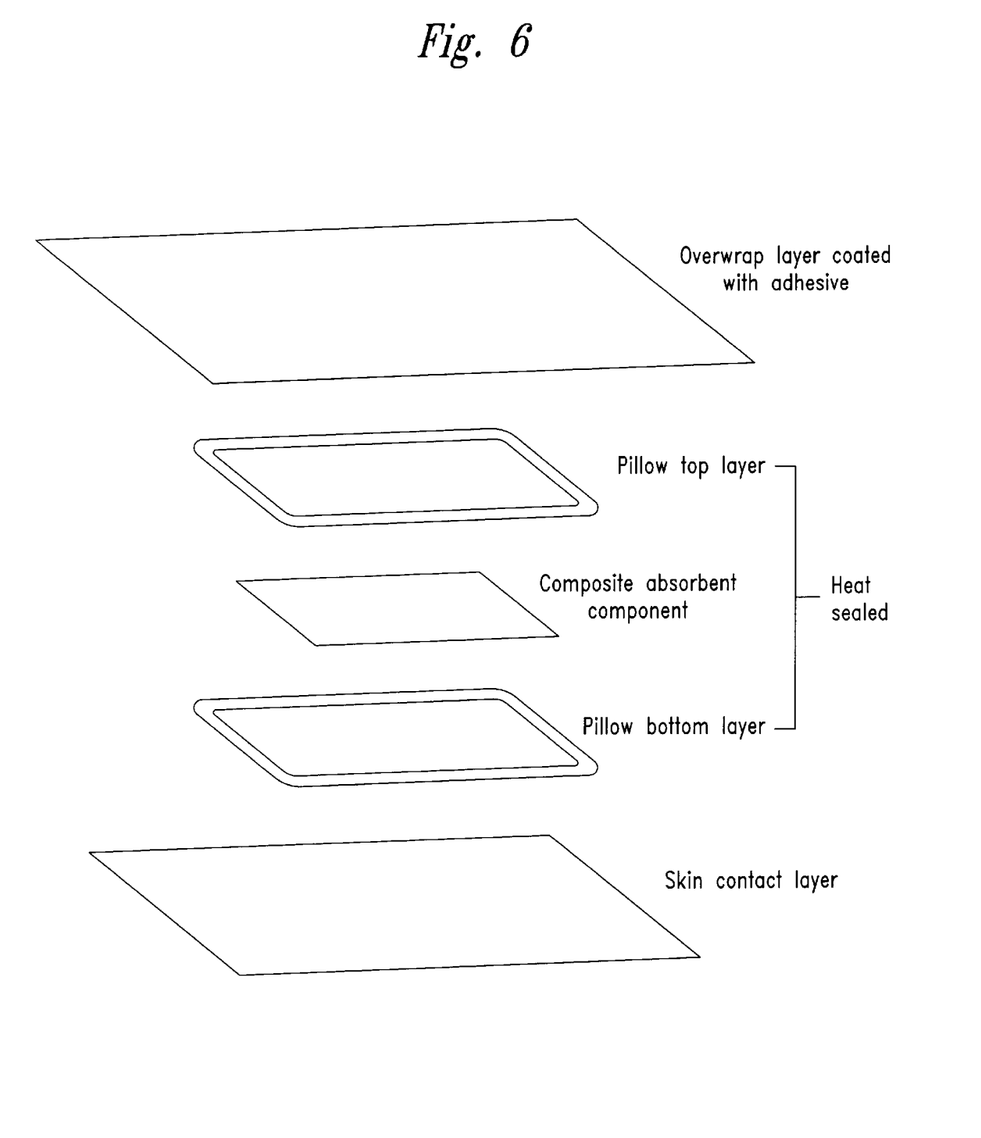
FIG. 6 shows the construction of a representative wound dressing containing a central island composed of a sachet containing absorbent dried hydrogel particles.

Sachet Containing Absorbent Hydrogel Particles Combined With Binding Agents and Plasticizers A 7 g absorbent layer composed of dried hydrogel particles approximately 2 inches square by 1/16 inches high was prepared as described in Example 5. It was then heat sealed between two sheets of porous non-woven nylon material approximately 2 and ½ inches square to form a sachet or pouch. A 4 and ½ inch square sheet of polyurethane foam was coated with 2 mil. of medical grade adhesive. The sachet described above was adhered to the adhesive coated foam concentrically and covered concentrically with a 3 and ½ inch square sheet of LDPE mesh. Silicone treated release paper was then applied to the adhesive side and the dressing was packaged. This dressing is illustrated in FIG. 6.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

What is claimed is:

1. An absorbent dressing for absorbing exudate from a wound, comprising a plurality of absorbent dried hydrogel particles sealed within a porous container, wherein the porous container is non-adherent to the wound and the absorbent hydrogel particles, after absorbing the exudate, remain sealed within the porous container, wherein the hydrogel particles are in a form selected from powders, granules, cylindrical pellets, spheres, spheroids, and mixtures thereof, and wherein the porous container comprises at least two square, rectangular, circular or oval compartments, wherein each compartment contains a plurality of absorbent dried hydrogel particles sealed therein.

2. The absorbent dressing of claim 1 wherein the dried hydrogel particles are polyacrylonitrile hydrogel particles.

3. The absorbent dressing of claim 1 wherein the hydrogel particles are selected from polyacrylic acid, polyacrylamide, poly-2-hydroxyethylmethacrylate, polyethylmethacrylate, polypropyleneglycolmethacrylate, poly-N-vinylpyrrolidone, polymethylmethacrylate, polyglycidylmethacrylate and polyglycolmethacrylate hydrogel particles.

4. The absorbent dressing of claim 1 wherein the dried hydrogel particles are selected from absorbent silicones and absorbent polyurethane hydrogel particles.

5. The absorbent dressing of claim 2 wherein the polyacrylonitrile hydrogel particles are prepared by base hydrolysis of polyacrylonitrile aquagel.

6. The absorbent dressing of claim 2 wherein the polyacrylonitrile hydrogel particles are prepared by acid hydrolysis of polyacrylonitrile aquagel.

7. The absorbent dressing of claim 5 wherein the quench point of the acid hydrolysis ranges from 4 to 12.

8. The absorbent dressing of claim 5 wherein the quench point of the acid hydrolysis is about 12.

9. The absorbent dressing of claim 5 wherein the quench point of the acid hydrolysis is about 6.

10. The absorbent dressing of claim 1 wherein the hydrogel particles are in the form of cylindrical pellets.

11. The absorbent dressing of claim 10 wherein the cylindrical pellets have a length ranging from 0.5–2 mm and a diameter of about 1 mm.

12. The absorbent dressing of claim 1 wherein the hydrogel particles are in the form of spherical particles.

13. The absorbent dressing of claim 12 wherein the spherical particles have a diameter ranging from 0.5–mm.

14. The absorbent dressing of claim 1 wherein the porous container is made from a material selected from nylon, cotton, polyester, polypropylene, polyvinylacetate, and mixtures thereof.

15. The absorbent dressing of claim 14 wherein the porous container is polyethylene.

16. The absorbent dressing of claim 1 wherein the porous container is of a shape selected from a square, rectangle, circle, and oval.

17. The absorbent dressing of claim 1 further comprising an adherent portion for adhering the dressing to the wound.

18. The absorbent dressing of claim 1 further comprising a protective portion for protecting the wound.

19. The absorbent dressing of claim 1 further comprising an agent for delivery to the wound.

20. The absorbent dressing of claim 19 wherein the agent is selected from a wound healing agent.

21. The absorbent dressing of claim 20 wherein the wound healing agent is selected from a growth factor, antiseptic agent, anti-microbial agent, vitamin, micronutrient, antibiotic, antifungal, and mixtures thereof.

22. The absorbent dressing of claim 21 wherein the micronutrient is selected from a copper-containing and zinc-containing compound or complex.

23. The absorbent dressing of claim 1 further comprising an odor control agent.

24. The absorbent dressing of claim 23 wherein the order control agent is activated charcoal.

25. The absorbent dressing of claim 1 wherein the absorbent dried hydrogel particles are in the form of powders.

26. The absorbent dressing of claim 25 wherein the powders are formed into a sheet.

27. The absorbent dressing of claim 26 wherein the sheet further comprises a component selected from a binder, plasticizer and mixtures thereof.

28. The absorbent dressing of claim 17 wherein the adherent portion and absorbent dressing, taken together, form an island dressing.

* * * * *